(12) United States Patent
Matsutani et al.

(10) Patent No.: US 6,444,651 B1
(45) Date of Patent: Sep. 3, 2002

(54) ANTIMICROBIAL AGENTS FOR EUCARYOTIC MICROORGANISMS AND METHODS OF GROWTH SUPPRESSION OF EUCARYOTIC MICROORGANISMS USING THESE AGENTS

(75) Inventors: Keiko Matsutani; Yasuki Fukuda, both of Gifu; Mizuo Yajima, Tokyo; Wataru Hashimoto; Kousaku Murata, both of Kyoto, all of (JP)

(73) Assignee: Asama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/591,019

(22) Filed: Jun. 9, 2000

Related U.S. Application Data

(63) Continuation-in-part of application No. 08/994,580, filed on Dec. 19, 1997, now Pat. No. 6,096,719.

(30) Foreign Application Priority Data

Sep. 3, 1997 (JP) .............................................. 9-254190

(51) Int. Cl.$^7$ ................... A61K 31/7088; A61K 31/711
(52) U.S. Cl. ....................... 514/44; 536/23.1; 536/23.7; 536/24.1; 536/24.5
(58) Field of Search ........................... 514/44; 536/23.1, 536/23.7, 24.1, 24.5

(56) References Cited

U.S. PATENT DOCUMENTS 4,560,678 A * 12/1985 Ranson ........................ 514/44

OTHER PUBLICATIONS

Yi et al., J. Immunology, 1996, vol. 157, pp. 5394–5402.*
Schorderet et al., PNAS, 1992, vol. 89, pp. 957–961.*
Shimizu et al., Gene, 1997, vol. 205, pp. 103–107.*

* cited by examiner

*Primary Examiner*—David Guzo
(74) *Attorney, Agent, or Firm*—Flynn, Thiel, Boutell & Tanis, P.C.

(57) ABSTRACT

An antimicrobial composition for eucaryotic microorganisms and method of suppressing the growth of eucaryotic microorganisms requires a procaryotic DNA extract. The antimicrobial composition is effective against numerous types of eucaryotic microorganisms and can be safely added to food and cosmetic products.

3 Claims, No Drawings

ANTIMICROBIAL AGENTS FOR EUCARYOTIC MICROORGANISMS AND METHODS OF GROWTH SUPPRESSION OF EUCARYOTIC MICROORGANISMS USING THESE AGENTS

This is a continuation-in-part of Ser. No. 08/994,580, filed Dec. 19, 1997, now U.S. Pat. No. 6,096,719.

FIELD OF THE INVENTION

This invention relates to the protection from infection by eucaryotic microorganisms.

BACKGROUND OF THE INVENTION

Chemically synthesized antimicrobial agents which suppress the growth of eucaryotic microorganisms are well known but many of these agents raise concerns about their safety. It is also known that some antibiotics produced by microorganisms suppress the growth of eucaryotic microorganisms. However, these agents cannot be applied to foods, cosmetics and industrial chemicals due to regulatory controls. Extracts of various spices or garlic have been recognized to have antimicrobial activity but they have peculiar odors, even at low doses, and therefore, their application has been limited.

SUMMARY OF THE INVENTION

This invention is directed to safe antimicrobial agents originating from natural sources which are able to suppress the growth of eucaryotic microorganisms and can be applied to foods, cosmetics, pharmaceuticals and industrial chemicals.

As a result of a search for natural sources which are able to suppress the growth of yeasts and molds, it was found that DNA obtained from procaryotic microorganisms suppressed the growth of eucaryotic microorganisms significantly. It is believed that there is a difference in the functional roles between DNA extracted from procaryotic microorganisms and DNA of eucaryotic microorganisms because of differences of methylation and frequency of CG dinucleotide sequences in both microorganisms and that the difference may relate to one of the self-protective functions in procaryotic microorganisms against eucaryotic microorganisms.

The present invention is directed to antimicrobial agents which are effective against eucaryotic microorganisms, in which a major component of the antimicrobial agent is DNA extracted from procaryotic microorganisms and a method of suppressing the growth of eucaryotic microorganisms by the addition of the inventive antimicrobial agent.

DETAILED DESCRIPTION OF THE INVENTION

In the present invention, the procaryotic micro-organisms include all Gram-positive and Gram-negative bacteria.

The Gram-positive bacteria include those of the Bacillus genus such as *B. subtilis, B. cereus., B. megaterium, B. mesentericus, B. licheniformis, B. sphaericus, B. alvei, B. natto* and *B. circulans*; lactic acid bacteria such as Lactobacillus plantarum, *L. acidophilus, L. brevis, L. casei, L. delbrueckii, L. fermentum* and *L. helveticus* and *Lactococcus lactis, Leuconostoc mesenteroides, L. dextranicum, Pediococcus pentosaceus, P. acidilactici, Streptococcus faecium* and *Str. faecalis*; and Cocci such as *Micrococcus luteus, M. flavus, M. roseus, Staphylococcus aureus* and *S. epidermidis*.

The Gram-negative bacteria include *Aeromonas hydrophila, Alcaligenes faecalis, Enterobacter cloacae, K-lebsiella peumoniae, Escherichia coli, Proteus vulgaris, Pseudomonas aeruginosa, Ps. fluorescens, Ps. aureofaciens, Salmonella Typhimurium, Sal. Enteritidis, Serratia marcescens* and *Vibrio*.

When a foodstuff is to be prevented from spoiling or being mixed with a mycotoxin, DNA of a lactic acid bacteria or B. natto, a species of *B. substilis* used for natto food, or DNA of Escherichia coli can be used in the invention.

DNA of procaryotic microorganisms can be used in the invention to protect materials other than food, plants and living things from eucaryotic microorganisms.

The invention can be used to prevent spoilage of food products and fruit by molds or enzymes produced by the eucaryotes. Eucaryotic microorganisms against which the present invention is effective include those which produce mycotoxins, such as Aflatoxin, Ochratoxin, Sterigmatocystin, Penicillium toxin and Fusarium toxin. Diseases by eumycetes that can be treated by the invention include infections by, for example, trichophyton and candida, plant pathology and fish pathology. Molds on houses, furniture, in the kitchen, bathroom and on floors can be treated by the present invention.

Procaryotic DNA degraded by restriction enzymes also can be used and the size of the DNA is preferably at least 1,000 bases in order to show the growth suppressing effects. It is also favorable for the DNA to contain a large number of CG dinucleotide sequences in the molecule. A CG dinucleotide sequence means that C and G are successive bases in the nucleotide sequence of the procaryotic DNA.

It is preferable that the procaryotic DNA include CG dinucleotide sequences occurring at a frequency of at least two times, more preferably at least 17 times, as in the DNA of the eucaryotic microorganisms.

As eucaryotic microorganisms that are treated by the present invention, yeasts such as *Saccharomzyces cerevisiae* and *Candida albicans* and filamentous fungi such as *Aspergillus niger* and *Aspergillus fumigatus* are examples.

EXAMPLE 1

As an example of extracting DNA from procaryotic microorganisms, Bacillus natto, IFO 3336, is cultivated in a 500 ml-volume Erlenmeyer flask containing 200 ml L-Broth medium (0.1% glucose, 0.5% yeast extract, 1.0% peptone and 0.5% NaCl, pH 7.2) at 30° C. for 30 hours. The cells are harvested by centrifugation (8,000 rpm, 10 minutes) and washed twice with a 0.85% saline solution.

The cell suspension in 40 ml of distilled water is incubated with 20 mg of lysozyme at 37° C. for 20 minutes and then heated to 65° C. to break down the cells. Cold ethanol (−20° C.) is gradually added to the suspension and about 500 mg of insoluble DNA is obtained by means of winding the DNA onto a glass rod. The obtained DNA is washed with 70%, 80% and 90% ethanol solutions, respectively, and dried in vacuo. Thus, highly purified DNA is prepared as a solution containing 2 mg DNA per ml of distilled water.

When *Saccharomyces cerevisiae* is cultivated in an SD medium in the presence of 1 mg/ml DNA for yeast culture (2.0% glucose and 0.67% amino acid free-yeast nitrogen bases) in the presence of the DNA obtained as described above at 30° C., for 24 hours, growth of the yeast is completely suppressed. However, the growth of *Saccharomiyces cerevisiae* is not suppressed in the medium in the absence of the procaryotic DNA.

EXAMPLE 2

A. Preparation of the DNA

Procaryotic microorganisms, *Bacillus natto* (IFO 3336) and *Escherichia coli* k-12 (IFO 14410), were incubated in a 500 ml-volume Erlenmeyer flask containing 200 ml of L-Broth culture medium (0.1% glucose, 0.5% yeast extract, 1.0% peptone and 0.5% NaCl, pH 7.2) at 30° C., respectively. After 30 hours, the cells of each bacterium were harvested and washed with a 0.085% saline solution twice and then the cells were suspended in 40 ml of distilled water. After the addition of 20 mg of lysozyme to the suspension, the temperature was increased to 65° C. to degrade the cells. 500 mg of DNA insolubized by the gradual addition of −20° C. ethanol was obtained by means of winding onto a glass rod.

B. Tests for Growth Suppression of Yeasts

DNA obtained from each bacterial strain described above was washed by an ethanol solution of which the concentration was increased from 70 to 80% followed by 80 to 90% and dried in vacuo. Thus, the highly purified DNA was obtained as a solution containing 2 mg DNA per ml of distilled water.

A yeast, *Saccharomyces cerevisiae* FT-1 (Journal of Fermentation and Bioengineering, 70, 275, 1990) which was obtained from K. Kimura, was cultivated in 5 ml of the SD medium (2.0% glucose and 0.67% yeast nitrogen-base, amino acid-free) at 30° C. for 24 hours. The DNA obtained from each bacterial strain was added to four flasks containing 100 ml of the SD medium. The final concentration of the DNA in each flask was 0, 0.2, 0.4, 0.6 and 0.8 mg/ml, respectively. To these media containing different concentration of the DNA, 0.1 ml of the yeast strain cultivated as described above was inoculated. Each SD medium containing the DNA was cultivated at 30° C. for 24 hours on a shaker and the yeast cells grown in the medium were harvested and washed with 0.85% saline. The cells were suspended in 10-folds, 100-folds and 1,000-folds volume of a 0.85% saline solution, respectively, and 0.1 ml each of the cell suspension was spread on a YDP agar plate medium (2% glucose, 2% peptone, 1% yeast extract and 1.5% agar, pH 5.0). After cultivation for one to two days at 30° C., the number of colonies grown on the plate medium was counted. The results are shown in Tables 1 and 2.

TABLE 1

DNA from *Bacillus natto*

| Concentration of DNA | 0 | 0.2 | 0.4 | 0.6 | 0.8 |
|---|---|---|---|---|---|
| Number of yeast cells | $1.2 \times 10^8$ | $8.0 \times 10^6$ | $1.4 \times 10^4$ | $2.0 \times 10^3$ | $2.0 \times 10^3$ |

TABLE 2

DNA from *E. coli* K-12

| Concentration of DNA | 0 | 0.2 | 0.4 | 0.6 | 0.8 |
|---|---|---|---|---|---|
| Number of yeast cells | $2.3 \times 10^8$ | $1.0 \times 10^6$ | $7.8 \times 10^4$ | $1.1 \times 10^3$ | $1.0 \times 10^3$ |

These results showed that the addition of higher than 0.4 mg/ml DNA of *B. natto* or *E. coli* K-12 strongly suppressed growth of the yeast.

EXAMPLE 3

A. Preparation of DNA

Two ml of the solution of E. coli DNA (10 mg) prepared as described in Example 2 were put into 4 test tubes, respectively, and then 3 times in volume of cold ethanol (−20° C.) was added. After 24 hours kept at 20° C., DNA was precipitated by centrifugation at 1,000 rpm for 10 minutes and the supernatant was discarded. The DNA precipitated was dried in vacuo.

Two ml of the reaction mixture for a restriction enzyme, EcoRI, (all enzymes used here were made by Takara Shuzo Co., Ltd., in Japan) containing 50 mM of Tris-HCl at a pH of 7.5, 10 mM of $MgCl_2$, 1 mM dithiothreitol and 100 mM NaCl were poured into a test tube to dissolve the DNA. Two 2 ml quantities of the reaction mixture for Hind III containing 10 mM of Tris-HCl pH 7.5, 10 mM of $MgCl_2$, 1 mM of dithiothreitol and 50 mM of NaCl were poured into two test tubes to dissolve the DNA. Subsequently, 10,000 U of each restriction enzyme was added to each test tube and incubated at 37° C. for two hours.

To one of the test tubes which were reacted with Hind III, two times the volume of cold ethanol (−20° C.) was added again, and the mixture was kept at −20° C. for a day. After centrifugation at 10,000 for 10 minutes, the DNA was precipitated and dried in vacuo. The reaction mixture for DNase (100 mM of sodium acetate, pH 5.0 and 0.5 mM of $MgSO_4$) was added to dissolve DNA and then the solution was incubated with 1,000 U of DNase I at 15° C. for two hours. The molecular size of the DNA degraded by these restriction enzymes was approximately 2 to 3,000 bases on the average.

B. Tests for Growth Suppression of Yeast

A yeast, *Saccharomyces cerevisiae* FT-1 (J. of Fermentation and Bioengineering 70, 275, 1990) was cultivated in 5 ml of the SD medium (2.0% glucose and 0.67% yeast nitrogen-base amino acid free) at 30° C. for 24 hours. The DNA solution prepared as described above was added to 100 ml of the SD medium in which the concentration of DNA was 0.4 mg/ml and the precultured yeast was inoculated at the size of 1/1000.

The yeast cell number was determined by optical density measured spectrophotometrically at 610 nm using a HITACHI Spectrophotometer, U-1100, after the yeast was cultivated for 24 hours in a shaker. Table 3 shows the growth suppression of the yeast by the DNA degraded using each enzyme.

TABLE 3

| | Cell Growth measured by O.D. |
|---|---|
| No DNA Added | 1.45 |
| DNA (No restriction enzyme added) | 0.11 |
| DNA (Degraded by EcoRI) | 0.62 |
| DNA (Degraded by HindIII) | 0.58 |
| DNA (Degraded by HindIII and DNase) | 1.21 |

These results indicated that the DNA degraded by restriction enzymes exhibited a weaker growth-suppressing activity. However, the activity of the DNA degraded by both EcoRI and DNase was higher than that without the DNA.

The data of Table 3-1 is obtained in the same manner as that of Table 3, showing that the antimicrobial effect can be obtained by CG dinucleotide sequences.

TABLE 3-1

| | Cell growth |
|---|---|
| Chemically synthesized oligonucleotide containing CG motif | 0.06 |
| Chemically synthesized oligonucleotide containing no CG motif | 0.93 |

EXAMPLE 4

Tests for Growth Suppression of Filamentous Fungus

After addition of the DNA obtained from E. Coli and that from B. natto into 5 ml of the SD medium (2.0% glucose, 0.67% yeast and nitrogen-base amino acid free, pH 5.2), in which the final concentration of the DNA was 0.2 mg/ml, respectively, a filamentous fungus, Aspergillus niger (IFO 4034) precultured in the SD agar medium was inoculated with an inoculate loop into the SD medium containing the DNA, and cultivated at 30° C. for 12, 24, 36 and 48 hours, respectively, in a shaker.

The mycelia of A. niger were obtained after filtration of the cultured broth through a filter-paper (Advantec No. 5) and the wet weight (gram) of the mycelia which did not pass through the paper was determined with an Electric balance, TOP FX-320.

Table 4 shows the growth suppression of each DNA.

TABLE 4

| Culture period (hrs) | 12 | 24 | 36 | 48 |
|---|---|---|---|---|
| No DNA added (mg/ml) | 0.2 | 2.3 | 3.7 | 4.8 |
| E. coli DNA | 0.01 | 0.1 | 0.2 | 0.3 |
| B. natto DNA | 0.01 | 0.1 | 0.1 | 0.2 |

These results indicated that each DNA sample suppressed the growth of the fungi for 48 hours cultivation in contrast with that of no DNA added.

EXAMPLE 5

Preservative Tests for a Sauce for Grilled Meats

Two percent in volume of water was added to a commercially available sauce for grilled meats made by Ebara-Shokuhin Co., Ltd., in Japan (the concentration of NaCl was 7.3% after addition of water), and 0.02% or 0.04% of the DNA prepared from B. natto was further added to the sauce. In order to test the preservative effects of the DNA, the sauce was kept at 30° C. for the times indicated. The result is shown in Table 5.

TABLE 5

| Days in Preservation | 0 | 5 | 9 | 10 | 15 | 25 | 30 | 45 |
|---|---|---|---|---|---|---|---|---|
| No DNA added | – | – | ++ | | | | | |
| 0.02% DNA | – | – | – | – | – | + | | |
| 0.04% DNA | – | – | – | – | – | – | – | + |

–: no change  +, ++: increased gas volume

The addition of 0.02 to 0.04% DNA was recognized to protect the sauce from yeast. + shows a slightly increased volume. ++ shows a visibly increased volume.

EXAMPLE 6

A commercially available noodle soup (made by Ninben Co., Ltd. in Japan) was diluted three folds in volume with water (the concentration of NaCl was 2.8% after the dilution). The DNA of E. coli prepared as described in Example 2 was added to the soup up at the level of 0.01 or 0.04%. The result is shown in Table 6.

TABLE 6

| Hours in Preservation | 0 | 12 | 24 | 36 | 48 | 60 | 72 | 84 | 96 |
|---|---|---|---|---|---|---|---|---|---|
| No DNA added | – | – | – | – | ++ | | | | |
| 0.01% DNA | – | – | – | – | – | – | + | | |
| 0.04% DNA | – | – | – | – | – | – | – | – | + |

– no change, + turbid, ++ turbid and increased volume

The DNA was shown to be effective on preservation of the noodle soup.

EXAMPLE 7

Tests for the Growth Inhibition of Pathogenic Eucaryotic Microorganisms

The minimum inhibitory concentrations (MIC) of B. natto DNA and E. coli DNA to human pathogenic eucaryotic microorganisms were determined as shown below in Table 7.

TABLE 7

| | MIC (%) | |
|---|---|---|
| | B. natto DNA | E. coli DNA |
| Candida albicans (TIMM0239) | 0.02 | 0.02 |
| Trichoderma spp. | 0.02 | 0.02 |
| Aspergillus niger (IAM2004) | 0.03 | 0.03 |
| Cladosporium spp. | 0.03 | 0.03 |
| Fusarium spp. | 0.04 | 0.04 |
| Mucor spp. | 0.02 | 0.02 |
| Penicillium spp. | 0.02 | 0.02 |

Medium used: Potato dextrose medium
Culture conditions: 25° C.,
1 to 3 weeks (filamentous fungi)
48 hours (yeasts)

The DNA was shown to inhibit the growth of typical human pathogenic eucaryotic microorganisms at concentrations of 0.02 to 0.04%.

In the same manner as Example 7, tests for growth inhibition of Aflotoxin-producing eucaryotic microorganisms were conducted and results are shown in Table 7-1.

TABLE 7-1

| | MIC (%) | |
|---|---|---|
| | B. natto DNA | E. coli DNA |
| Aspergillus flavus* | 0.03 | 0.03 |
| Aspergillus narasiticus* | 0.03 | 0.03 |
| Aspergillus achraceus* | 0.03 | 0.03 |
| Penicillium viridicatum* | 0.02 | 0.02 |
| Aspergillus versicolor | 0.03 | 0.03 |

EXAMPLE 8

The inhibitory effect of the DNA on the growth of plant pathogenic and fish pathogenic eucaryotic microorganisms was examined as shown in Table 8.

TABLE 8

|  | MIC (%) | |
| --- | --- | --- |
|  | B. natto DNA | E. coli DNA |
| Fusarium oxysporum f. sp. | 0.03 | 0.03 |
| Pythium ultimun | 0.02 | 0.02 |
| Rhizoctonia solani | 0.02 | 0.02 |
| Plasmodiophora brassiciae | 0.02 | 0.02 |
| Phytophthora spp. | 0.03 | 0.03 |
| Helicobasidium mompa | 0.02 | 0.02 |
| Saproregnia spp. | 0.03 | 0.03 |

Medium used: Potato dextrose medium
Culture conditions: 25° C., 7 days (fungi)
48 hours (yeasts)

The DNA inhibited the growth of typical plant pathogenic eucaryotic microorganisms at the levels of 0.02 to 0.03%.

EXAMPLE 9

Application for Cosmetics (Preservation Tests for Milky-Lotion Type Hair Tonics)

A milky-lotion type hair tonic was prepared using the components described below. It was manufactured under the open system since microbial infection from the air was expected.

| (A) Purified jojoba oil | 10.8% |
| --- | --- |
| Benzyl nicotinate | 2 |
| Lanolin | 2 |
| Isopropyl-myristate | 2.5 |
| Polyoxyethylene cetylalcohol | 1.8 |
| Sorbitan monostearate | 0.8 |
| (B) Triethanol amine | 1% |
| Glycerine | 4 |
| Deionized water | 75 |
| Flavours | Proper Quantity |

The oil phase (A) and aqueous phase (B) were heated to 85° C., respectively. Then, (A) and (B) were mixed and agitated to emulsification at the same temperature. A hair tonic was prepared after the mixture was cooled down to normal temperature.

The hair tonic prepared was poured into a bottle with 0.03% of the DNA. The bottle was sealed and kept at 37° C. for preservation tests. 0.1% Ethyl p-hydroxy benzoate was added to the hair tonic as a control instead of the DNA. The result is shown in Table 9.

TABLE 9

| Days | 0 | 7 | 14 | 21 | 28 |
| --- | --- | --- | --- | --- | --- |
| Control | — | — | + |  |  |
| DNA | — | — | — | — | + |

+: Fungi appeared

This result indicated that addition of 0.03% of the DNA was effective in the protection of a milky-lotion type hair tonic from fungal infection.

EXAMPLE 10

Preparation of an Agent for External Application

A preparation for skin application was produced according to the following recipe.

| E. Coli DNA | 1.0% |
| --- | --- |
| Glycerin | 5.0% |
| Propylene glycol | 4.0% |
| Oleyl alcohol | 0.1% |
| Ethanol | 5.0% |
| Benzoic acid | 0.05% |
| Purified water | 84.9% |

E. Coli DNA (Example 3), glycerin and propylene glycol were added to, and dissolved in, purified water. Meanwhile, oleyl alcohol and benzoic acid were dissolved in ethanol at room temperature. This ethanol solution was added to that aqueous solution, and solubilized. The mixture was heated at 90° C. for 20 minutes, filtered, and then put into a bottle.

EXAMPLE 11

Therapy with 1% Bacterial DNA Ointment in Dermatophyte Skin Infections

Clinical efficacy and safety of once-daily application for 35 days of 1% DNA ointment, prepared according to Example 10, in the treatment of interdigital tinea pedis and vesicular tinea pedis were studied.

Mycological investigation, signs and symptoms of infection were rated and any adverse events occurring during the study were recorded.

Analysis on efficacy and safety was conducted with respect to 57 patients with interdigital tinea pedis and 27 patients with vesicular tinea pedis. Results of the final global efficacy evaluation are shown in Table 10.

TABLE 10

Final global efficacy evaluation

| Type of disease | Inter-digital Type | Vesicular Type | Total |
| --- | --- | --- | --- |
| Markedly effective | 22 | 8 | 30 |
| (%) | (38.6) | (29.6) | (35.7) |
| Effective | 20 | 11 | 31 |
| (%) | (35.1) | (40.7) | (36.9) |
| Slightly effective | 10 | 4 | 14 |
| (%) | (17.5) | (14.8) | (16.7) |
| Ineffective | 5 | 4 | 9 |
| (%) | (8.8) | (14.3) | (10.7) |
| Total | 57 | 27 | 84 |
| (%) | (100) | (100) | (100) |
| Markedly effective + | 42 | 19 | 61 |
| Effective | (73.7) | (70.3) | (72.6) |
| (%) |  |  |  |
| Markedly effective + | 52 | 23 | 75 |
| Effective + | (91.2) | (85.2) | (89.3) |
| Slightly effective |  |  |  |
| (%) |  |  |  |

The overall efficacy rate ("markedly effective"+ "moderately effective") determined in the final global efficacy rating was 72.6% and 73.7% for interdigital tinea pedis and 70.3% for vesicular tinea pedis. Minimal adverse reactions, such as contact dermatitis, were observed in 2 of 84 patients. Dermal symptoms such as blisters and pustules showed marked improvement 3 weeks after starting the treatment. These findings show that bacterial DNA ointment is an effective and safe agent which can be recommended for the treatment of interdigital and vesicular tinea pedis.

EXAMPLE 12

Application for Agricultural Chemicals

Natsu-no-Kaori, trademark, a cucumber manufactured by Tohoku Co., Ltd., was sowed in a greenhouse in November.

The germinated nursery stocks were planted in the greenhouse in December. 10 stocks of an untreated lot and 10 stocks of a treated lot were tested. In January, at the treated lot, a 4% solution of DNA extract having 5% DNA was sprayed on the surface of the cucumbers leaves once every ten days. At the time of the beginning of the harvesting of the cucumbers in February, no generation of mildew at the treated lot was confirmed. On the contrary, all ten stocks of the untreated lot had mildew disease. After that, at the treated lot, the DNA extract solution was sprayed over the leaves once a month. As a result, it was confirmed that mildew was not generated on all ten stocks of the treated lot until June when the harvest came to an end.

EXAMPLE 13

Effect of Preventing Fish Disease

Forty Green Neon, tropical fish, were divided into two groups each consisting of 20 fish, and each group was bred in a 450×240×300 mm tank containing 250 mm depth of water. B. natto DNA, prepared in the same way as Example 1, was added to a test tank in an amount of 300 ppm. As a control, the other tank had no addition. To both tanks, one drop of a suspension of Saprolegnia ferax, mold, was added and the water in the tanks was contaminated.

After two weeks, the number of morbid fish due to the mold was counted to find that 8 out of 20 fish were ill in the control tank, although there was no fish that was ill in the test tank.

EXAMPLE 14

Clinical Efficacy of 1% Corynebacterium Glutamicum DNA Gelatinous Preparation for Tinea Pedis A preparation containing 1% DNA for skin application was produced according to EXAMPLE 10. However, the DNA used in this preparation was produced from the bacterial cells of Corynebacterium glutamicum ATCC 12435 in place of E. coli DNA of EXAMPLE 10. The gelatinous DNA preparation was applied two times a day, first in the morning and secondly before going to bed, to patients with interdigital tinea pedis and vesicular tinea.

The period of clinical treatment was 6 weeks. Patients were examined every 2 weeks for their dermal findings and mycological evaluation by direct microscopic examination and fungal cultivation tests.

Criteria for efficacy evaluation was graded into 5 grades. As for cutaneous symptoms such as Itching, Redness, Blister pustule and Scale, they were graded as Markedly improved, Improved, Slightly improved, Unchanged and Aggravated. As for mycological evaluation, Markedly effective (Negative both in microscopic examination and fungal cultivation), Effective (Negative in either of the two examinations), Slightly effective (Positive in both fungal tests but numbers of fungal cells were diminished), Ineffective (Unchanged) and Aggravated. The number of patients used for analysis were 79 (53 patients of interdigital tinea pedis and 26 patients of vesicular tinea pedis). The number of males and females were 37 and 42, respectively. The mean age were 51.1±3.2. The causative agents detected by a culture test were Tricophyton rubrum (19 cases) and Tricophyton mentagrophytes (31 cases).

The average treatment periods were 4.4±1.3 weeks for interdigital type tinea pedis and 4.6±1.0 weeks for vesicular tinea pedis. The final clinical evaluation of 79 patients conducted at the final $6^{th}$ week of the treatment period was summarized in Table 11.

TABLE 11

| | Final Clinical Evaluation | | | | | | |
|---|---|---|---|---|---|---|---|
| Type of disease | Markedly improved (%) | Improved (%) | Slightly improved (%) | Unchanged (%) | Total | Markedly improved + Improved % | Markedly improved + Improved + Slightly improved % |
| Interdigital type | 20 (37.7) | 19 (35.8) | 12 (22.6) | 2 (3.8) | 53 (100) | 73.5 | 96.1 |
| Vesicular type | 8 (30.8) | 12 (46.2) | 4 (15.4) | 2 (7.7) | 26 (100) | 77.0 | 92.4 |
| Total | 28 (35.4) | 31 (39.2) | 16 (20.3) | 3 (3.7) | 79 (100) | 74.6 | 94.9 |

The efficacy rate (markedly improved and improved) 5 in dermal findings was 74.6% and 73.5% for interdigital type and 77.0% for vesicular type.

The result of the final mycological evaluation by direct microscopic examination performed after the completion of the 6 week treatment period is summarized 10 in Table 12.

TABLE 12

| | Final Mycological Evaluation (Direct microscopic examination) | | |
|---|---|---|---|
| Type of disease | Total | Positive (%) | Negative (%) |
| Interdigital type | 53 | 14 (26.4) | 39 (73.6) |
| Vesicular type | 26 | 5 (19.2) | 21 (80.8) |
| Total | 79 | 19 (24.1) | 60 (75.9) |

As shown in Table 12, the detection rate of fungus became negative in 39 out of 53 patients, i.e. 73.6%, of interdigital tinea pedis and 22 of 26 patients, i.e. 80.8%, of vesicular tinea pedis. Accordingly, the total 5 negative rate changed from 0/79 (i.e., 0%) before treatment to 60/79 (i.e., 75.9%) after treatment. The final global efficacy evaluation is shown in Table 13.

TABLE 13

Final Global Efficacy Evaluation

| Type of disease | Markedly effective (%) | Effective (%) | Slightly effective (%) | Ineffective (%) | Total | Markedly effective + effective % | Markedly effective + effective + slightly effective % |
|---|---|---|---|---|---|---|---|
| Interditital type | 20 (37.7) | 18 (33.9) | 10 (18.9) | 5 (9.4) | 53 (100) | 71.6 | 90.5 |
| Vesicular type | 8 (30.8) | 12 (46.2) | 4 (15.4) | 2 (0) | 26 (100) | 77.0 | 92.4 |
| Total | 28 (35.4) | 30 (38.0) | 14 (17.7) | 7 (8.9) | 79 (100) | 73.4 | 91.1 |

The overall efficacy rate (markedly effective+moderately effective) determined in the final global efficacy rating was 73.4%, 71.6% for interdigital tinea pedis and 77.0% for vesicular tinea pedis. A minimal adverse reaction, contact dermatitis, was observed in 1 of 79 patients. Dermal symptoms such as blisters and pustules showed marked improvement 2 weeks after starting the treatment. From these findings, it was concluded that prokaryotic DNA preparation is an effective and safe topical agent which can be recommended for the treatment of dermatophytes infection.

Although examples of the present invention have been presented for the purpose of explaining the present invention, the present invention is by no way limited thereto and is deemed to cover all modifications and substitutions that would be obvious to one of ordinary skill in the art.

What is claimed is:

1. A method of topically treating a human infected with a eucaryotic microorganism which causes tinea pedis comprising the step of contacting the microorganism with a pharmacologically effective amount of procaryotic microorganism DNA comprising a nucleotide sequence containing at least 1,000 bases.

2. The method of claim 1, wherein the procaryotic microorganism is *Escherichia coli*.

3. The method of claim 1, wherein the procaryotic microorganism is *Corynebacterium glutamicum*.

* * * * *